(12) United States Patent
Hall et al.

(10) Patent No.: US 7,482,906 B2
(45) Date of Patent: Jan. 27, 2009

(54) BOBIN ASSEMBLY FOR A DRIVING ASSEMBLY USED IN A PERSONAL CARE APPLIANCE

(75) Inventors: Scott E. Hall, Issaquah, WA (US); Craig D. Hanela, North Bend, WA (US); Richard K. Taylor, Fall City, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 11/501,373

(22) Filed: Aug. 8, 2006

(65) Prior Publication Data

US 2006/0267419 A1 Nov. 30, 2006

Related U.S. Application Data

(62) Division of application No. 10/139,293, filed on May 2, 2002, now Pat. No. 7,122,921.

(51) Int. Cl.
*H01F 27/30* (2006.01)

(52) U.S. Cl. .......................................... 336/208; 320/2
(58) Field of Classification Search .................. 336/208
See application file for complete search history.

(56) References Cited

U.S. PATENT DOCUMENTS

| | | | |
|---|---|---|---|
| 2,650,993 A | 9/1953 | Brown | |
| 3,300,664 A | 1/1967 | Boyles | |
| 3,418,552 A * | 12/1968 | Holmes | ...................... 320/108 |
| 3,549,990 A * | 12/1970 | Hochheiser | .................. 323/345 |
| 3,840,795 A | 10/1974 | Roszyk | |
| 4,374,354 A * | 2/1983 | Petrovic et al. | ............. 320/108 |
| 5,189,751 A | 3/1993 | Giuliani et al. | |
| 5,565,833 A | 10/1996 | Leet et al. | |
| 5,706,542 A * | 1/1998 | Okada | ........................ 15/22.1 |
| 6,836,917 B2 * | 1/2005 | Blaustein et al. | ............. 15/22.1 |
| 2001/0024152 A1 | 9/2001 | Miyazaki | |

FOREIGN PATENT DOCUMENTS

DE 4020305 A1 1/1992

(Continued)

*Primary Examiner*—Elvin G Enad
*Assistant Examiner*—Joselito Baisa

(57) ABSTRACT

A first aspect of the disclosure concerns a driving assembly for a power toothbrush which includes a drive member, specifically an E-core electromagnet, a driven member which is responsive to the action of the drive member and a workpiece mounted on the distal end of the driven member. The drive assembly includes an interface registration member, to one end surface portion of which is secured the end face of E-core electromagnet, another portion of which is configured to produce a selected registration of the driven member and the driving assembly, and still another portion of which is configured to produce a selected registration of the interface member relative to the handle of the toothbrush.

A second aspect of the disclosure concerns a split bobbin assembly for an electrical coil portion of an electromagnet in a power toothbrush. The split bobbin assembly includes a first portion which mates with a portion of the appliance which is exposed to the operating environment of the appliance and is made from a material which has sufficient chemical-resistant properties for tolerance of exposure to the environment. A second portion of the split bobbin is made from a material which is resistant to heat so as to withstand soldering of the electrical coil wires to the terminal pins positioned in a base part of the bobbin assembly. Connecting elements on the first and second portions join the two portions together.

7 Claims, 2 Drawing Sheets

FOREIGN PATENT DOCUMENTS

| | | |
|---|---|---|
| DE | 19602642 A1 | 7/1997 |
| EP | 0138014 A1 | 4/1985 |
| EP | 1009008 A2 | 6/2000 |
| GB | 1031350GB A | 6/1966 |

* cited by examiner

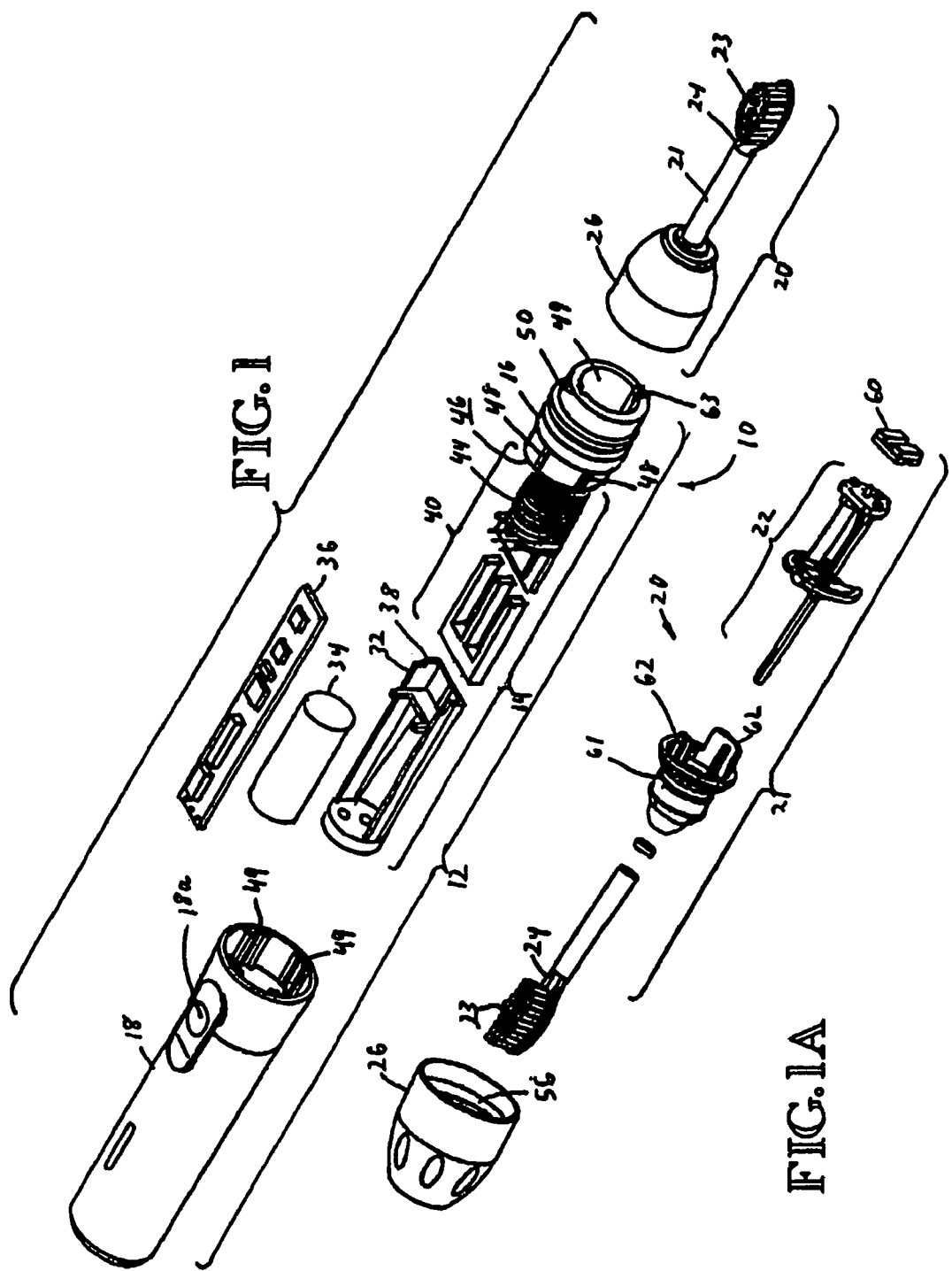

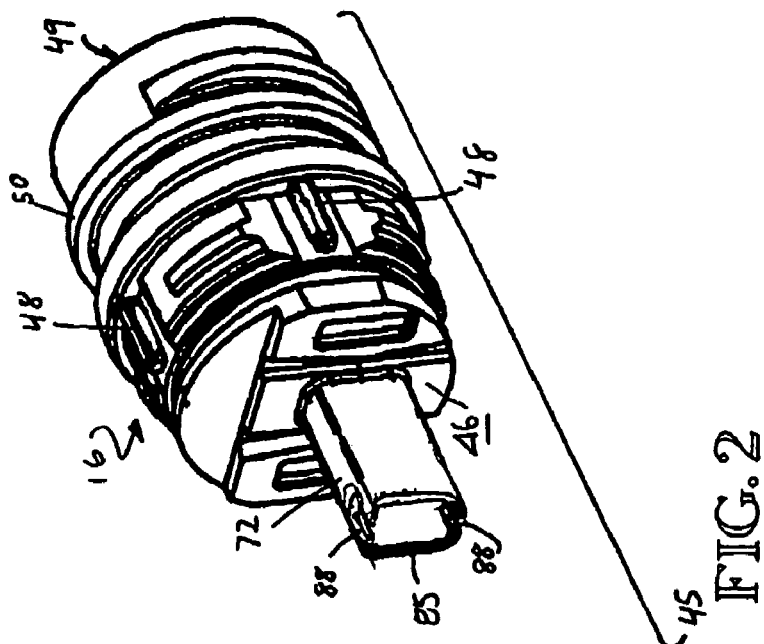
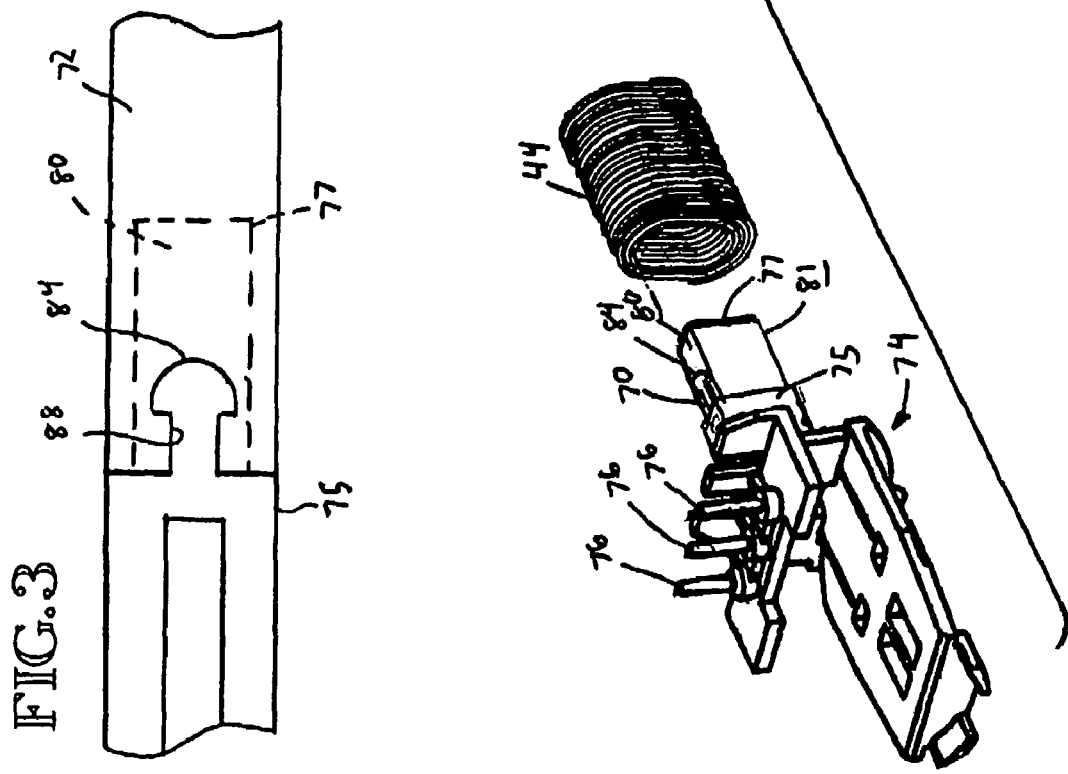

BOBIN ASSEMBLY FOR A DRIVING ASSEMBLY USED IN A PERSONAL CARE APPLIANCE

CROSS REFERENCE TO RELATED APPLICATIONS

This is a divisional of Application Ser. No. 10/139,293, filed May 2, 2002 now U.S. Pat. No. 7,122,921.

TECHNICAL FIELD

This invention relates generally to internal drive assemblies for small appliances such as power toothbrushes, and more specifically concerns first an interface member which registers a drive assembly and a driven member relative to a handle of the toothbrush, thereby precisely aligning the drive assembly and the driven element, and also concerns a bobbin member used in a winding portion of such a drive assembly.

BACKGROUND OF THE INVENTION

In the manufacture of small appliances, such as power toothbrushes, it is important that the drive assembly portion thereof be in precise physical alignment relative to the driven member which, for instance, could be a pivoted arm on which a workpiece (a brushhead) is mounted. In a typical known approach, a carrier is assembled with a number of internal parts of the appliance mounted thereon. The carrier is then installed into a handle housing, typically from a bottom (proximal) end thereof, over which is secured a cover. The driven member is mounted to the other (distal) end of the handle housing. Reliable alignment of the driving assembly with the driven member is thus often difficult because the interface between the driving assembly and the driven member is at the opposite end of the handle housing from the point of installation of the driving assembly.

Misalignment, due to relative sideways or even rotational movement between the driving assembly and the driven element readily occurs. The interface between the driving assembly and the driven element is typically part of the housing, thus making the housing a critical element in the proper operation of the appliance. A spring or other part is often used to hold the driving assembly to the interface, but this adds to the overall expense, size and complexity of the device. Due to manufacturing and tooling considerations, this bottom loading approach also requires that the housing be larger at the bottom than at the top, which is undesirable from an aesthetic and ergonomic standpoint.

In another aspect of the invention, a driving assembly may include an electromagnet having a center core winding. The core member which holds the winding, referred to as a bobbin, is secured at one end to the electromagnet frame, which includes the electrical pin connections/terminals to the coil winding and the battery, while the other end is secured to or is a part of a mounting/interface element which is secured to the handle portion of the appliance and to which is secured a head portion of the device.

The mounting element and the portion of the bobbin secured thereto is exposed to the operating environment of the appliance; e.g. toothpaste and water or other dentifrices for a power toothbrush. The portion of the bobbin secured to the mounting element thus must also be of a material which can stand exposure to the operating environment of the appliance, such as toothpaste and water for a power toothbrush, as well as being attractive to the consumer including the capability of being colored.

The portion of the bobbin attached to or part of the frame must be heat-resistant to withstand the elevated temperatures encountered during soldering of the wire terminations from the core winding to the pin connections which also receive wire connections from the battery. This portion of the bobbin must also be high strength, to withstand the coil winding process.

Unfortunately, no single material has all of the above capabilities/characteristics. Hence, there have been design compromises with respect to the construction of winding bobbins in power toothbrushes in particular, either in the design of the bobbin itself and/or its relationship with the other portions of the drive assembly. Further, a single part requires a complex and hence expensive manufacturing tool. In this aspect of the invention, it is desirable to have a bobbin assembly which satisfies all of the above-described requirements.

SUMMARY OF THE INVENTION

Accordingly, a first aspect of the present invention is a driving assembly for a small power appliance comprising: a drive member having a distal end portion, wherein the drive member in operation moves a driven member assembly in a specific motion; a driven member assembly which includes a workpiece at a distal end thereof and which moves in response to the action of the drive member; and an interface registration member, having a plurality of interface portions, wherein a first interface portion has fixedly connected thereto, in a pre-established position, the distal end portion of the drive member and wherein the drive member assembly is mounted in a fixed relationship with interface member at a second interface portion thereof, so as to produce a reliable, fixed alignment between the drive member and the driven member assembly.

Another aspect of the invention is an electrical coil portion of a driving assembly used in a power appliance, a first portion which is mated with a part of the appliance exposed to the operating environment of the appliance, wherein the first portion is made from material which can withstand exposure to the operating environment; a second opposing portion which is mated with a base part of the driving assembly and is made from a material which is sufficiently heat resistant as to permit attachment of coil wires to terminal pin located in the base part and has sufficient strength to withstand the coil being wound therearound; and connecting elements on the first and second portions to join the first and second portions together.

BRIEF DESCRIPTION OF THE DRAWING

FIG. 1 is an exploded view of a power toothbrush appliance, including the internal assembly configuration of the present invention.

FIG. 1A is an exploded view of a portion of the power toothbrush of FIG. 1.

FIG. 2 is an exploded view showing the bobbin assembly of the present invention.

FIG. 3 is a top view of a portion of the assembly of FIG. 2.

BEST MODE FOR CARRYING OUT THE INVENTION

FIG. 1 shows a small appliance, in particular a power toothbrush, in an exploded view generally at 10. In general, appliance 10 includes a handle portion 12 which includes an internal drive assembly 14 with an interface registration element 16 at one end thereof, and a housing 18 for the handle portion. The interface element 16 is connected in a fixed physical relationship to an upper end of housing 18, as described in more detail below.

The appliance also includes a head assembly 20 which, in the embodiment shown, includes a workpiece assembly 21, which in turn includes a driven member 22. The driven member is joined to a brushhead arm 25 which has a brushhead 23 located at a distal end 24 thereof. The head assembly 20 is fixed to the interface element 16 in a manner described below. A nut 26 secures the head assembly 20 to interface element 16 by means of a threaded relationship. Other attachment means, such as clamping or individual attachment elements could, however, be used.

More specifically, the internal drive assembly 14 includes a carrier element 32 to which holds a battery 34 and a PCB board 36 which carries the electronic drive circuitry for the toothbrush. Extending from the distal end 38 of carrier 32 is a drive member 40, which for example, is an E-core electromagnet which includes an E-core stack 42, with a central coil winding 44. The E-core stack extends from an electromagnet frame 43 which is attached to and extends from carrier 32. Winding 44 is wound on a bobbin element 45 of the drive member 40. The distal end of the bobbin 45 is fixedly connected to or an integral part of a proximal end surface 46 of interface element 16, while the proximal end of bobbin 45 is fixedly connected to or an integral part of frame 43. The free ends of E-core stack 42 are also secured to the proximal end surface 46 of interface element 16. During manufacture of the appliance, the entire internal drive assembly is built onto the interface element. At that point it is possible to test the drive assembly for proper function.

Around the exterior periphery of interface element 16 in a first, lower portion thereof are a plurality of registration elements 48, such as narrow raised portions, which fit into corresponding slots 49 in the interior surface of housing 18 near the top end thereof. During manufacture the open top housing 18 is installed over the completed internal drive assembly including the carrier 32 and is secured to the interface element 16 with the registration elements 48 fitting into the corresponding slots 49 in the interior housing surface.

This results in a fixed physical relationship between the interface element 16 and the handle housing, i.e. the interface element and the drive member secured thereto are registered relative to the housing, in a known physical relationship. Thus, it is possible to attach the housing directly to the interface element and maintain a direct, aligned relationship of the drive member and the driven element to the interface element. This is an important structural aspect of the present invention, specifically, the accurate physical positioning of the interface element 16 relative to the drive member 40 and housing 18.

Although the embodiment shown includes individual registration elements in the form of raised portions to accomplish and maintain this relationship, other arrangements could be used, such as clamps and/or a threaded connection. The use of registration elements and mating slots has proven to be reliable and effective, however.

An upper portion of interface element 16 is hollow and defines a cup-like interior 49. On the exterior upper periphery of interface element 16 is a threaded portion 50, which is configured to receive a mating threaded portion 56 on the internal surface of nut 26. The workpiece assembly 21 includes, in the embodiment shown, a movable brushhead arm 25 with a brushhead 23 on the distal end 24 thereof. The brushhead arm is moved by a driven member 22. On the proximal end of driven member 22 are permanent magnets 60, which interact cooperatively with the electromagnetic drive member in the handle to produce a back and forth motion of the rear end of the driven member 22. In the embodiment shown, this is a side-to-side motion with a slight arc. The resulting motion of brushhead 23 will vary, depending upon the rest of the workpiece assembly, which could include a motion conversion element changing the drive motion from arcuate side-to-side to rotary, as is the case for the apparatus of FIG. 1A. However, this is not necessary to the present invention.

The workpiece assembly also includes a mounting member 61, which includes registration elements 62-62 which fit into corresponding slots 63 in the interior surface of the upper portion (the cup-like interior 49) of interface element 16, so that the driven member 22, with the permanent magnets 60, has a fixed registration relationship relative to interface element 16 and hence also to the drive member 40. Nut 26 is threaded on to the exterior upper portion of the interface element 16 to produce a completed appliance.

Interface element 16 thus accomplishes a reliable and repeatable fixed physical relationship between the drive member 40, i.e. the electromagnet, and the driven element 22 which has permanent magnets 60 mounted at the rear end thereof, and which is joined to brushhead arm 21. The housing 18 acts mainly as a cover and is hence not critical to the operation of the drive arrangement of the appliance. However, the alignment of the housing in the interface element is important in certain applications, such as the positioning of the switch contacts in the carrier and the over-molded on/off button 18a on the housing as well as the alignment of any LED's on the PCB board with a window on the housing for battery level readings, etc.

In confined spaces, such as a power toothbrush, this precise alignment between a drive member and a driven element is quite important for efficient operation. The present invention accomplishes this objective in an easy, repeatable, reliable manner through the use of the interface element and a top loading drive assembly connected thereto.

In one embodiment discussed above, an electromagnet is used as a drive member for an appliance such as a toothbrush. The electromagnet includes, as discussed above, winding 44 which is wound on bobbin 45. In the embodiment shown, the bobbin with the winding is positioned over the center stack of the electromagnetic E-core. Other winding and bobbin arrangements are certainly possible and the one shown is for illustration only.

The bobbin of the present invention is "split", in that it comprises two separate portions 70 and 72 which are then joined together. One portion 70 extends into and is part of a frame or base part 74 of the drive element. The base part 74 includes three pin connections 76-76 which form the terminal connections for the winding and the wire connections from the battery. The base part 74 must thus be able to withstand high temperatures. Portion 70 of the split bobbin is made from the same material as the base part. This material must also be able to withstand the pressure of the wire tension during winding of the coil therein, which is typically several pounds. The material for bobbin portion 70 and base part 74 must be strong enough that it will not crush even when it is relatively thin.

The other portion 72 of the split bobbin, extends into or is part of the rear surface of interface element 16. It is made from the same material as the interface element. The interface element 16 itself is made from a material which is chemically resistant to the environmental conditions of the appliance, such as toothpaste and/or other chemical compounds for dental treatment, which may be encountered during operation of the appliance. Further, the material must have the capability of presenting a good cosmetic finish for aesthetic purposes, including the ability to be colored to match the other exposed portions of the toothbrush.

The first portion 70 of the split bobbin, which extends from or is an integral part of the frame or base part 74 of the drive element, includes a first section 75 which extends from base part 74 and a second section 77 which extends from the end of the first section 75. The first section 75 is slightly larger in exterior size than the second portion 77. In the embodiment shown, the first section 75 is approximately ⅜ inches long, while the second section is approximately ½ inch long. The second section 77 has slightly smaller dimensions (approximately ¹⁄₃₂-inch around its periphery relative to the first section 75. Extending outwardly (approximately ¹⁄₃₂ inch) from the top and bottom surfaces 80, 81 are ears 84-84 which each have a slight, outward bulge at a forward end thereof. The two ears, however, have slightly different configurations, as discussed in more detail below. Both portions 70 and 72 are rectangular in configuration and hollow. Bobbin portion 72 is approximately ⅝ inches long and has internal dimensions to receive the second section 77 of the first bobbin portion 70. Bobbin portion 72 also comprises two sections along its length. A first section is adjacent the interface element 16, while the other section extends from the first section to the end of portion 72. The external dimensions of the two sections are the same, but their internal diameters are different. The internal opening of the second, outboard section is smaller, resulting in a stronger section than the first section.

Extending inwardly from the outer edge 85 of the second bobbin portion 72 in the upper and lower opposed surfaces thereof, respectively, are slots 88 (one in each surface) which are configured to receive ears 84-84 of the first bobbin portion. The ears 84-84, with the slight outward bulge thereof, can be snapped into slots 88-88. As indicated above, the ears 84-84 are slightly different in configuration; the two slots 88-88 are also slightly different, arranged to mate with their associated ears 84-84. As a result, the two parts can be joined in only one particular orientation. Each ear uniquely fits its associated slot and not the other. When the two portions are snapped together, the edge of the larger section 75 of portion 70 acts as a stop for the edge 85 of portion 72. This arrangement produces uniform length of the resulting bobbin assembly. The two bobbin portions are held together securely by the ear/slot combinations, although they can be pulled apart with the use of sufficient force.

The coil wire is wound around the two joined portions of the bobbin, extending from the base part of the drive element to the rear surface 46 of the interface element, holding the two bobbin portions 70 and 72 firmly together. In detail, the firm joinder of the bobbin portions is accomplished as follows: First, the ears 84-84 are positioned in the slots 88-88. The two portions thus resist being pulled apart. Further, the second, outboard section of bobbin portion 72, overlaps outboard section 77 of portion 70 when the two portions are snapped together. The coil is then wound around the two portions. The tension of the coil winding is sufficient to compress the second outboard section of portion 72 into firm contact with section 77 of portion 70. This compression greatly increases the frictional force between the two portions, thus greatly increasing the force that is required to separate them. Sections 77 and 75 of portion 70 are not deformed in any significant way since portion 70 is formed from a strong material. The outboard section of portion 72 is also not significantly deformed, since it has a small interior opening and overlaps section 77 of portion 70.

Hence, the split bobbin arrangement described and shown herein permits the use of a material at the interface end of the bobbin which meets all of the requirements of that portion of the bobbin, i.e. chemically resistant and aesthetically pleasing, and a second material at the other end of the bobbin which meets all of the requirements of that end of the bobbin, i.e. heat-resistant to permit soldering and high strength to withstand the coil winding process.

Accordingly, with the present structure, there need be no compromise relative to the materials used in the bobbin. The particular manner of joining the two portions 70 and 72 described herein is also significant, since dissimilar materials cannot be welded or glued reliably and the use of fasteners would increase the space required and increase the complexity of the assembly method. The split bobbin design in fact significantly simplifies the tooling needed for the bobbin. To have all of the needed features on a single part would result in a very complex tool; splitting the part into two portions results in two much simpler parts to tool and manufacture.

Accordingly, an internal assembly for a small power appliance such as a toothbrush has been described. In one aspect, a registration assembly has been described which provides the required alignment capability between a driving member and a driven element. This is particularly advantageous for confined space devices. With the top end load approach, all of the critical parts of the appliance are attached directly to the interface element. The interface element, the split bobbin coil and E-core laminated stack comprise the drive system. The carrier and the control circuit are also attached to the interface element. The brushhead assembly is directly attached to the upper (cup) side of the interface element by means of the nut element. Further, for those devices using an electromagnetic driver with a coil winding, a split bobbin arrangement has been described which meets the stringent and heretofore irreconcilable requirements of a bobbin structure which needs to be strong and heat-resistant, but also chemical resistant, capable of being exposed to the environment and aesthetically pleasing.

Although a preferred embodiment of the invention has been described for purposes of illustration, it should be understood that various changes, modification and substitutions can be made in the embodiment without departing from the spirit of the invention which is defined in the claims which follow.

What is claimed:

1. A bobbin assembly for an electrical coil portion of a driving assembly used in a power appliance, comprising:
    a first portion which is mated with a part of the appliance exposed to the external operating environment of the appliance, wherein the first portion is made from material which can withstand exposure to the external operating environment;
    a second, opposing portion which is mated with a base part of the driving assembly and is made from a material which is substantially different than the material comprising the first portion, sufficiently heat-resistant as to permit attachment of coil wires to terminal pins located in the base part and has sufficiently high strength to withstand the coil being wound therearound; and
    connecting elements on the first and second portions to join the first and second portions together, wherein the connecting elements interlock together such that the first and second portions define a complete, intergrated bobbin member around the exterior surface of which a single, continuous coil is thereafter wound.

2. An article of claim 1, wherein the connecting elements are so configured that when they are interlocked, they are resistant to being pulled apart.

3. An article of claim 2, wherein the connecting elements are so configured that when the coil is wound on them, resistance to being pulled apart is increased.

4. An article of claim 1, wherein the connecting elements are generally rectangular in cross-sectional configuration.

5. An article of claim 1, wherein the power appliance is a toothbrush, wherein the driving assembly is an E-core electromagnet, and wherein the electrical coil is wound around a middle portion of the E-core.

6. An article of claim 1, wherein the first and second portions each include one end wall of the integrated bobbin assembly and a portion of the remainder of the integrated bobbin assembly.

7. An article of claim 1, wherein a part of one of the first and second portions is insertable into a part of the other of the first and second portions.

* * * * *